United States Patent
Wang et al.

(10) Patent No.: US 9,594,038 B1
(45) Date of Patent: Mar. 14, 2017

(54) DEVICE AND METHOD FOR MEASURING SUPERCRITICAL CARBON DIOXIDE FRACTURING FLUID THROTTLING COEFFICIENT UNDER DIFFERENT VISCOSITIES

(71) Applicant: China University of Petroleum (East China), Qingdao, Shangdong (CN)

(72) Inventors: Jintang Wang, Shandong (CN); Baojiang Sun, Shandong (CN); Yun Liu, Shandong (CN); Zhiyuan Wang, Shandong (CN); Hao Li, Shandong (CN); Jianbo Zhang, Shandong (CN)

(73) Assignee: China University of Petroleum (East China), Shandong (CN)

( * ) Notice: Subject to any disclaimer, the term of this patent is extended or adjusted under 35 U.S.C. 154(b) by 0 days.

(21) Appl. No.: 15/270,594

(22) Filed: Sep. 20, 2016

(30) Foreign Application Priority Data

Sep. 30, 2015 (CN) .......................... 2015 1 0641282

(51) Int. Cl.
*G01N 25/00* (2006.01)
*E21B 43/24* (2006.01)

(52) U.S. Cl.
CPC .......... *G01N 25/00* (2013.01); *E21B 43/2405* (2013.01)

(58) Field of Classification Search
CPC ............................ G01N 25/00; E21B 43/2405
See application file for complete search history.

(56) References Cited

U.S. PATENT DOCUMENTS

| 2010/0032171 | A1  | 2/2010 | Bali et al. |
| 2011/0029273 | A1* | 2/2011 | Lovell ..................... E21B 47/10 702/130 |
| 2012/0237311 | A1* | 9/2012 | Dionne ............. B23Q 11/1061 409/135 |
| 2016/0161462 | A1* | 6/2016 | Iyer ......................... E21B 47/06 702/6 |

FOREIGN PATENT DOCUMENTS

| CN | 103196796 A | 7/2013 |
| CN | 103540308 A | 1/2014 |
| CN | 104101559 A | 10/2014 |

* cited by examiner

*Primary Examiner* — Hezron E Williams
*Assistant Examiner* — David Z Huang
(74) *Attorney, Agent, or Firm* — Calfee, Halter & Griswold LLP

(57) ABSTRACT

The present invention relates to a device and method for measuring supercritical carbon dioxide fracturing fluid throttling coefficient under different viscosities. The device for measuring supercritical carbon dioxide fracturing fluid throttling coefficient under different viscosities comprises a supercritical carbon dioxide fracturing fluid throttling coefficient measurement system and a supercritical carbon dioxide fracturing fluid viscosity adjustment apparatus; the supercritical carbon dioxide fracturing fluid throttling coefficient measurement system determines throttling coefficient of a high temperature and high pressure supercritical carbon dioxide fracturing fluid, and the supercritical carbon dioxide fracturing fluid viscosity adjustment apparatus determines viscosity of the high temperature and high pressure supercritical carbon dioxide fracturing fluid.

5 Claims, 2 Drawing Sheets

DEVICE AND METHOD FOR MEASURING SUPERCRITICAL CARBON DIOXIDE FRACTURING FLUID THROTTLING COEFFICIENT UNDER DIFFERENT VISCOSITIES

CROSS REFERENCE TO RELATED APPLICATIONS

This application claims priority to Chinese Application No. 201510641282.8, filed on Sep. 30, 2015, entitled "Device for measuring supercritical carbon dioxide fracturing fluid throttling coefficient under different viscosities", which is specifically and entirely incorporated by reference.

TECHNICAL FIELD

The present invention belongs to the technical field of unconventional oil and gas exploitation, and specifically relates to a device and method for measuring supercritical carbon dioxide fracturing fluid throttling coefficient under different viscosities.

BACKGROUND

Unconventional natural gas source includes coal-bed gas, shale gas, tight sandstone gas and water-soluble gas. Currently, the unconventional oil and gas resources have been played an important role in the global energy structure. In this country, the unconventional oil and gas resources have rich reserves, wide distribution and broad development prospects. The technical exploitable resource of the unconventional natural gas is up to $3.4 \times 10^5$ billion cubic meters, which is 1.8 times of the technical exploitable resource of the conventional natural gas.

However, the unconventional oil and gas resources are difficult to exploit and basically have characteristics of low porosity, low permeability, low pressure, and compact rock formation. Historical breakthrough of the shale exploitation technology is realized by combining the horizontal drilling technology and horizontal fracturing technology with the Barnett shale in Fort Worth Basin in Texas, US, and the single well exploitation cost is greatly reduced. Therefore, for the unconventional oil and gas reservoir, fracturing manner is mainly used for transform the oil and gas reservoir to improve the oil (gas) productivity index, thereby improving single well yield and stable yield validity. The conventional water base fracturing causes large damage to the shale oil and gas reservoir and causes severe secondary pollution in the solution, and severely affects the capacity increasing revamping effect of the solution, specifically in the following aspects: (1) damage to the stratum caused by the fracturing fluid polymer; (2) damage caused to the stratum due to unreasonable drainage speed; and (3) damage easily caused to the water sensitive stratum.

The supercritical carbon dioxide injection fracturing includes producing a supercritical carbon dioxide jet flow by the injection fracturing apparatus, injecting through the casing and the reservoir rock to form a perforation hole and then performing fracturing. The supercritical carbon dioxide injection fracturing has the following characteristics: no free water, conveying proppant agents to form propped fractures, no free water and solid residues in the propped fractures, being completely suitable for water sensitive reservoir and removing the damage to the reservoir. Therefore, the supercritical carbon dioxide injection fracturing can improve the flow conductivity of the unconventional oil and gas reservoir and is one of the effective means for realizing effective commercial exploitation. The supercritical carbon dioxide fracturing fluid is a mixed substance formed by dissolving the thickening agent into the supercritical carbon dioxide. The fracturing fluid flows by the injection fracturing apparatus to create throttling effect, causing the temperature to reduce and affecting the physical property and injection fracturing effect of the fracturing fluid. Currently, with the influence of the temperature, pressure and the viscosity of the fracturing fluid, the rules of the throttling effect of the supercritical carbon dioxide fracturing fluid are relatively complex with few test data. The viscosity of the supercritical carbon dioxide fracturing fluid changes with the temperature and pressure. There is no systematic explanation for the principle of the throttling process, so that it is a difficulty in the supercritical carbon dioxide injection fracturing exploitation of the unconventional oil and gas reservoir.

SUMMARY OF THE INVENTION

In order to overcome the shortcoming of the prior art, the present invention provides a device for measuring supercritical carbon dioxide fracturing fluid throttling coefficient under different viscosities for quickly measuring the throttling coefficients of the supercritical carbon dioxide fracturing fluid at different temperatures, and under different pressures and fracturing fluid viscosities so as to perform system analysis to the rules of the throttling effect of the supercritical carbon dioxide fracturing fluid and provide experimental basis for the supercritical carbon dioxide injection fracturing design and theoretical research.

In order to solve the above-mentioned technical problem, the present invention uses the following technical solution:

A device for measuring supercritical carbon dioxide fracturing fluid throttling coefficient under different viscosities comprises a supercritical carbon dioxide fracturing fluid throttling coefficient measurement system and a supercritical carbon dioxide fracturing fluid viscosity adjustment apparatus; the supercritical carbon dioxide fracturing fluid throttling coefficient measurement system determines a throttling coefficient of a high temperature and high pressure supercritical carbon dioxide fracturing fluid, and the supercritical carbon dioxide fracturing fluid viscosity adjustment apparatus determines viscosity of the high temperature and high pressure supercritical carbon dioxide fracturing fluid.

Compared to the prior art, the present invention has the following beneficial effects:

(1) it can realize measurement of the throttling coefficient of the supercritical carbon dioxide fracturing fluid within a large pressure and temperature range, and can obtain the rules of throttling effect of the supercritical carbon dioxide fracturing fluid under different viscosities;

(2) the apparatus operation is simple, the method is easy to implement, and the feasibility is high;

(3) the measurement method is scientific, and can realize parameter measurement with a high precision.

In the Figure: 11, constant speed and constant pressure pump; 12, static mixer; 13, mass flow meter; 14, intermediate container; 141, intermediate container pressure meter;

142, intermediate container thermometer; 15, first screwing valve; 16, thermal insulation throttling measurement apparatus; 161, perforated plate; 161a, hole channel; 161b, outer wall; 161c, proppant particle; 162, first pressure meter; 163, first thermometer; 164, second pressure meter; 165, second thermometer; 17, back pressure control apparatus; 18 second screwing valve; 20, thermostatic water bath, 21, third screwing valve; 22, measurement pipeline segment; 221, first differential pressure sensor; 23, supercritical carbon dioxide booster apparatus; 231, carbon dioxide gas source inlet screwing valve; 24, thickening agent injection apparatus; 241, thickening agent inlet screwing valve; 25, supercritical carbon dioxide fracturing fluid unloading screwing valve; G1, first pipeline; and G2, second pipeline.

DETAILED DESCRIPTION

Figure 1:
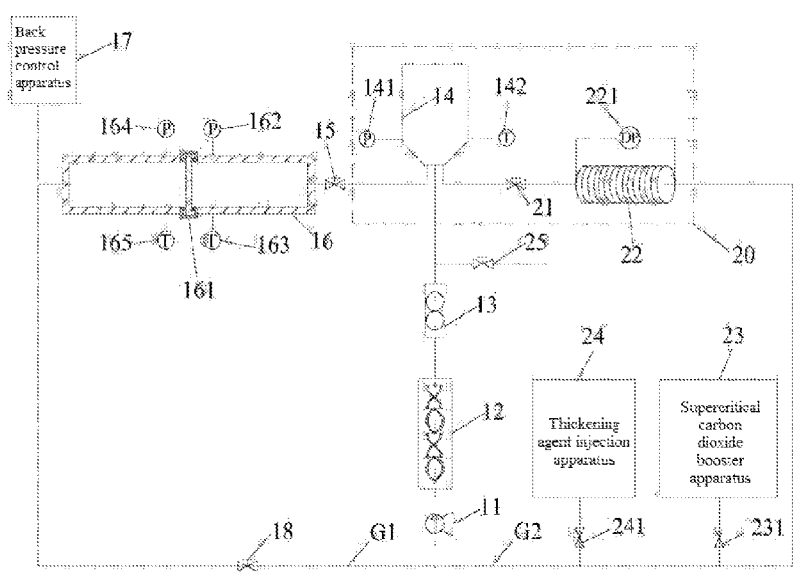
FIG. 1 is a schematic diagram of a device for measuring supercritical carbon dioxide fracturing fluid throttling coefficient under different viscosities.

As shown in FIG. 1, the device for measuring supercritical carbon dioxide fracturing fluid throttling coefficient under different viscosities comprises a supercritical carbon dioxide fracturing fluid throttling coefficient measurement system and a supercritical carbon dioxide fracturing fluid viscosity adjustment apparatus; the supercritical carbon dioxide fracturing fluid throttling coefficient measurement system determines throttling coefficient of a high temperature and high pressure supercritical carbon dioxide fracturing fluid, and the supercritical carbon dioxide fracturing fluid viscosity adjustment apparatus determines viscosity of the high temperature and high pressure supercritical carbon dioxide fracturing fluid.

The supercritical carbon dioxide fracturing fluid throttling coefficient measurement system may include a constant speed and constant pressure pump 11, a static mixer 12, a mass flow meter 13, an intermediate container 14, a first screwing valve 15, a thermal insulation throttling measurement apparatus 16, a back pressure control apparatus 17 and a second screwing valve 18. The constant speed and constant pressure pump 11, a static mixer 12, a mass flow meter 13, an intermediate container 14, the first screwing valve 15, the thermal insulation throttling measurement apparatus 16, and the second screwing valve 18 are connected successively through a pipeline to form a closed circulation loop. The back pressure control apparatus 17 which is connected to the pipeline between the thermal insulation throttling measurement apparatus 16 and the second screwing valve 18 may control the back pressure of the supercritical carbon dioxide fracturing fluid through the throttling measurement apparatus. The supercritical carbon dioxide fracturing fluid unloading screwing valve 25 is connected to the pipeline between the mass flow meter 13 and the intermediate container 14 for unloading the supercritical carbon dioxide fracturing fluid in the pipeline.

The constant speed and constant pressure pump 11 provides power required for closed cycle for the supercritical carbon dioxide fracturing fluid, so that the fluid flows from the static mixer 12 to the intermediate container 14 via the mass flow meter 13. The supercritical carbon dioxide fracturing fluid flows into the constant speed and constant pressure pump 11 through the first screwing valve 15, the thermal insulation throttling measurement apparatus 16 and the second screwing valve 18. The static mixer 12 completely mixes and dissolves the thickening agent into the supercritical carbon dioxide to form the supercritical carbon dioxide fracturing fluid. The mass flow meter 13 is used for metering the mass flow of the supercritical carbon dioxide fracturing fluid. The intermediate container 14 is used for buffering storage of the supercritical carbon dioxide fracturing fluid.

The intermediate container 14 is placed in a thermostatic water bath 20. The intermediate container 14 is provided with an intermediate container pressure meter 141 and an intermediate container thermometer 142. The thermostatic water bath 20 heats the supercritical carbon dioxide fracturing fluid to reach the required temperature. The intermediate container pressure meter 141 measures the pressure in the intermediate container, and the intermediate container thermometer 142 measures the temperature in the intermediate container.

Figures 2A, 2B:
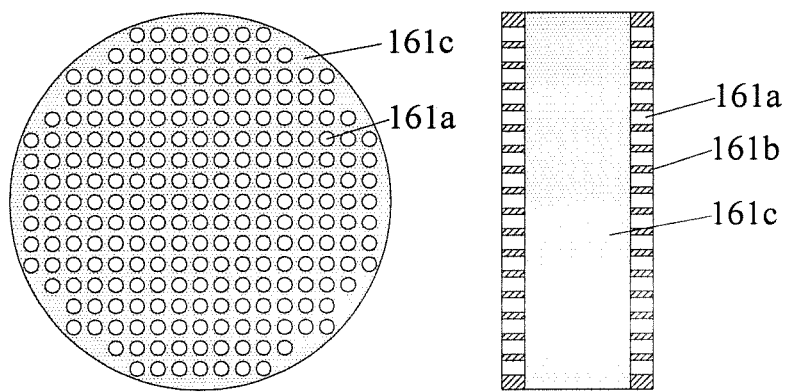
FIGS. 2A and 2B are schematic diagrams of detail view of perforated plate.

The thermal insulation throttling measurement apparatus 16 may include a cylindrical housing, a perforated plate 161, a first pressure meter 162, a first thermometer 163, a second pressure meter 164 and a second thermometer 165. The cylindrical housing has a length of 30 cm, an inner diameter of 5 cm, a wall thickness of 4 mm and is made of austenitic stainless steel material and coated with Sodium thermal insulation soft felt. As shown in FIGS. 2A and 2B, the perforated plate 161 is a perforated cylindrical cavity having a length of 2 cm and a diameter of 5.8 cm. The perforated plate 161 is filled with proppant particles 161c of 40-60 meshes. 100 hole channels 161a with a diameter of 0.2 mm are uniformly formed on the circular surface of the outer wall 161b of the perforated plate 161. The perforated plate 161 is located in the middle of the cylindrical housing and vertical to the axis of the cylindrical housing for providing a flow channel for the supercritical carbon dioxide fracturing fluid through the thermal insulation throttling measurement apparatus 16.

The first pressure meter 162, the first thermometer 163, the second pressure meter 164 and the second thermometer 165 are respectively disposed on two sides of the perforated plate 161 within the cylindrical housing. The first pressure meter 162 measures the pressure of the supercritical carbon dioxide fracturing fluid before adiabatic throttling. The first thermometer 163 measures the temperature of the supercritical carbon dioxide fracturing fluid before adiabatic throttling. The second pressure meter 164 measures the pressure of the supercritical carbon dioxide fracturing fluid after adiabatic throttling. The second thermometer 165 measures the temperature of the supercritical carbon dioxide fracturing fluid after adiabatic throttling.

The supercritical carbon dioxide fracturing fluid is pumped into the static mixer 12, the mass flow meter 13 and the intermediate container 14 by the constant speed and constant pressure pump 11, flows into the thermal insulation throttling measurement apparatus 16 via the first screwing valve 15 and passes by the second screwing valve 18 to form a closed circulation loop for measuring the supercritical carbon dioxide fracturing fluid throttling coefficient.

First pipeline G1 is the pipeline between the second screwing valve 18 and the constant speed and constant pressure pump 1.

The supercritical carbon dioxide fracturing fluid viscosity adjustment apparatus may include: a third screwing valve 21, a measurement pipeline segment 22, a supercritical carbon dioxide booster apparatus 23 and a thickening agent injection apparatus 24. The third screwing valve 21 is connected to a pipeline between the intermediate container 14 and the measurement pipeline segment 22 through a pipeline. The measurement pipeline segment 22 is connected to the first pipeline G1 via a second pipeline G2.

The measurement pipeline segment 22 is a copper coiler having an inner diameter of 4 mm, a wall thickness of 2 mm and a length of 8 m placed in the thermostatic water bath 20. The measurement pipeline segment 22 is provided with a measurement pipeline segment differential pressure sensor 221 for measuring the differential pressure that is produced when the supercritical carbon dioxide fracturing fluid flowing through the measurement pipeline segment 22.

The supercritical carbon dioxide booster apparatus 23 is coupled to the second pipeline G2 for providing the required experiment pressure for carbon dioxide. The supercritical carbon dioxide booster apparatus 23 is provided with a carbon dioxide gas source inlet screwing valve 231 for controlling carbon dioxide to enter into the supercritical carbon dioxide fracturing viscosity adjustment apparatus. The thickening agent injection apparatus 24 is coupled to the second pipeline G2 to pump the thickening agent into the high temperature and high pressure supercritical carbon dioxide pipeline. The thickening agent injection apparatus 24 is provided with a thickening agent inlet screwing valve 241 for controlling the thickening agent to enter into the supercritical carbon dioxide fracturing fluid viscosity adjustment apparatus. The supercritical carbon dioxide booster apparatus 23 and the thickening agent injection apparatus 24 are successively connected with the second pipeline G2 in a direction from the measurement pipeline segment 22 to the constant speed and constant pressure pump 11.

The supercritical carbon dioxide reaches the pressure required by the experiment through the supercritical carbon dioxide booster apparatus 23. The thickening agent injection apparatus 24 injects the thickening agent into the pipe through the second pipeline G2. The thickening agent is pumped into the static mixer 12 by the constant speed and constant pressure pump 11 and mixed to form a supercritical carbon dioxide fluid and form a closed flow circulation loop through the mass flow meter 13, the intermediate container 14, the third screwing valve 21 and the measurement pipeline segment 22 for adjusting the viscosity of the supercritical carbon dioxide fracturing fluid.

The measured data of the intermediate container pressure meter 141, the intermediate container thermometer 142, the first pressure meter 162, the first thermometer 163, the second pressure meter 164, the second thermometer 165 and the first differential pressure sensor 221 are collected by the data processing terminal in real time.

In the entire device, all the components and the pipelines withstand a pressure of 60 MPa and a temperature upper limit of 500 K, which can realize experimental measurement of supercritical carbon dioxide fracturing fluid throttling coefficient at a high temperature and under a high pressure.

A method for measuring supercritical carbon dioxide fracturing fluid throttling coefficient using the above-mentioned device includes the following steps:

(1) Creating a Supercritical Carbon Dioxide Cycle

Adjusting the thickening agent inlet screwing valve 241, the supercritical carbon dioxide fracturing fluid unloading screwing valve 25, the first screwing valve 15 and the second screwing valve 18 to be in a closed state; turning on the supercritical carbon dioxide booster apparatus 23, and adjusting the carbon dioxide gas source inlet screwing valve 231 and the third screwing valve 21 to be in an open state; and setting the thermostatic water bath 20 to adjust the temperature and the pressure of the experimental system to be the temperature and the pressure set for the experiment.

(2) Adding a Thickening Agent

Turning on a thickening agent injection apparatus, opening the thickening agent inlet screwing valve 241, pumping the thickening agent into the supercritical carbon dioxide fracturing fluid viscosity adjustment apparatus, wherein the thickening agent and carbon dioxide flow under the action of the constant speed and constant pressure pump 11, and the thickening agent is completely dissolved into the supercritical carbon dioxide in the static mixer 12; after the parameter is stable, measuring the viscosity of the supercritical carbon dioxide fracturing fluid.

(3) Calculating the Viscosity of the Supercritical Carbon Dioxide Fracturing Fluid Reading a pressure P of the intermediate container pressure meter 141, a temperature T of the intermediate container thermometer 142, a differential pressure $\Delta p$ of the first differential pressure sensor 221 and the reading of a mass flow quantity Q of the mass flow meter 13 from the data processing terminal, and calculating the viscosity $\mu$ of the supercritical carbon dioxide fracturing fluid:

$$\mu = \frac{uD\rho}{Re} \quad (1)$$

$$u = \frac{4Q}{\rho \pi D^2} \quad (2)$$

$$\rho_{CO_2} = \frac{PM_g}{ZRT} \quad (4)$$

$$Z^3 + (C-1)Z^2 + (A-2BC-B^2-B-C)Z + (BC+C-A)B = 0 \quad (5)$$

$$A = \frac{aP}{R^2 T^2} \quad (6)$$

$$B = \frac{bP}{RT} \quad (7)$$

$$C = \frac{cP}{RT} \quad (8)$$

$$\frac{1}{\sqrt{\lambda}} = -2.34 \times 1 \text{g} \left( \frac{\varepsilon}{1.72d} - \frac{9.26}{Re} \times 1 \text{g} \left( \left( \frac{\varepsilon}{29.36D} \right)^{0.92} + \left( \frac{18.35}{Re} \right)^{1.108} \right) \right) \quad (9)$$

$$\lambda = \frac{2D\Delta p}{\rho u^2 L} \quad (10)$$

Wherein $\mu$ is the viscosity of the supercritical carbon dioxide fracturing fluid, in Pa·s; u is the flow rate of the supercritical carbon dioxide fracturing fluid, in m/s; D is the diameter of the measurement pipeline segment 22, in m; ρ is the density of the supercritical carbon dioxide fracturing fluid, in kg/m³; Re is the Reynolds number of the supercritical carbon dioxide fracturing fluid (dimensionless); Q is the mass flow quantity of the supercritical fracturing fluid, in kg/s; $\rho_{CO2}$ is the density of the supercritical carbon dioxide gas, in kg/m$^3$; $x_{CO2}$ is the volume fraction of carbon dioxide in the fracturing fluid (dimensionless); $\rho_t$ is the density of the thickening agent, in kg/m$^3$; $x_t$ is the volume fraction of the thickening agent in the fracturing fluid (dimensionless); P is the pressure of the supercritical carbon dioxide gas, in MPa; $M_g$ is the molecular weight of the carbon dioxide, in kg/Kmol; Z is the compressibility factor of the supercritical carbon dioxide gas (dimensionless); R is the general gas constant 0.008314 MPa·m$^3$/(Kmol·K); T is the temperature of the supercritical carbon dioxide gas, in K; A, B and C are intermediate variables, the equations are as shown in formulae (6), (7) and (8), a=318101.19, b=26.82, c=25.01; λ is the coefficient of friction resistance of the supercritical carbon dioxide (dimensionless); ε is the absolute roughness, in m; ΔP is the differential pressure measured by the measurement pipeline segment differential pressure sensor 221, in Pa; and L is the length of the measurement pipeline segment 22, in m;

(4) Measuring the Throttling Coefficient $C_j$ of the Supercritical Carbon Dioxide Fracturing Fluid Closing the third screwing valve 21, opening the first screwing valve 15 and the second screwing valve 18, setting the inlet pressure of the throttling apparatus by the constant pressure and constant speed pump 11, and setting the outlet back pressure by the back pressure control apparatus 17; after the parameter is stable, reading a pressure $p_1$ of the first pressure meter 162, a pressure $p_2$ of the second pressure meter 164, a temperature $T_1$ of the first thermometer 163 and a temperature $T_2$ of the second thermometer 165 from the data processing terminal, and calculating the throttling coefficient C of the supercritical carbon dioxide fracturing fluid:

$$\Delta T' = T_1 - T_2 \quad (11)$$

$$\Delta p' = p_1 - p_2 \quad (12)$$

$$C_j = \frac{\Delta T'}{\Delta p'} \quad (13)$$

Wherein $C_j$ is the throttling coefficient of the supercritical carbon dioxide fracturing fluid, in K/Pa; $T_1$ is the temperature of the first thermometer 163, in K; $T_2$ is the temperature of the second thermometer 165, in K; $p_1$ is the pressure of the first pressure meter 162, in Pa; $p_2$ is the pressure of the second pressure meter 164, in Pa; ΔT' is the differential temperature before and after throttling, in K; Δp' is the differential pressure before and after throttling, in Pa.

By changing the viscosity of the supercritical carbon dioxide fracturing fluid of the experimental system, the rules of the throttling coefficient of the supercritical carbon dioxide fracturing fluid varied with the viscosity of the fracturing fluid can be researched. Thereby researching the throttling principle of the supercritical carbon dioxide fracturing fluid under different viscosities can be achieved and experiment basis for the supercritical carbon dioxide fracturing design and theoretical research can be provided.

What is claimed is:

1. A device for measuring a supercritical carbon dioxide fracturing fluid throttling coefficient under different viscosities, comprising: a supercritical carbon dioxide fracturing fluid throttling coefficient measurement system and a supercritical carbon dioxide fracturing fluid viscosity adjustment apparatus, wherein the supercritical carbon dioxide fracturing fluid throttling coefficient measurement system is configured to determine a throttling coefficient of a high temperature and high pressure supercritical carbon dioxide fracturing fluid, and the supercritical carbon dioxide fracturing fluid viscosity adjustment apparatus is configured to determine a viscosity of the high temperature and high pressure supercritical carbon dioxide fracturing fluid, wherein the supercritical carbon dioxide fracturing fluid throttling coefficient measurement system comprises a constant speed and constant pressure pump, a static mixer, a mass flow meter, an intermediate container, a first screwing valve, a thermal insulation throttling measurement apparatus, a back pressure control apparatus and a second screwing valve;

wherein the constant speed and constant pressure pump, the static mixer, the mass flow meter, the intermediate container, the first screwing valve, the thermal insulation throttling measurement apparatus, and the second screwing valve are connected successively through a pipeline to form a closed circulation loop;

the intermediate container is disposed in a thermostatic water bath, and the intermediate container is provided with an intermediate container pressure meter and an intermediate container thermometer;

the thermal insulation throttling measurement apparatus comprises a cylindrical housing, a perforated plate, a first pressure meter, a first thermometer, a second pressure meter and a second thermometer; the perforated plate is filled with proppant particles and uniformly formed with hole channels on the circular surface of an outer wall thereof;

the perforated plate is located in the middle of the cylindrical housing and vertical to the axis of the cylindrical housing; and the first pressure meter, the first thermometer, the second pressure meter and the second thermometer are respectively disposed on two sides of the perforated plate within the cylindrical housing;

the supercritical carbon dioxide fracturing fluid is pumped into the static mixer, the mass flow meter and the intermediate container by the constant speed and constant pressure pump, flows into the thermal insulation throttling measurement apparatus through the first screwing valve and passes by the second screwing valve to form a closed circulation loop for measuring the supercritical carbon dioxide fracturing fluid throttling coefficient; and a first pipeline is the pipeline between the second screwing valve and the constant speed and constant pressure pump;

the supercritical carbon dioxide fracturing fluid viscosity adjustment apparatus comprises: a third screwing valve, a measurement pipeline segment, a supercritical carbon dioxide booster apparatus and a thickening agent injection apparatus; the third screwing valve is on the pipeline between the intermediate container and the measurement pipeline segment;

and the measurement pipeline segment is connected with the first pipeline through a second pipeline; and the supercritical carbon dioxide booster apparatus is coupled to the second pipeline; the thickening agent injection apparatus is coupled to the second pipeline; and the measurement pipeline segment is provided with a measurement pipeline segment differential pressure sensor.

2. The device for measuring a supercritical carbon dioxide fracturing fluid throttling coefficient under different viscosities according to claim 1, wherein the cylindrical housing has a length of 30 cm, an inner diameter of 5 cm and a wall thickness of 4 mm, and is made of austenitic stainless steel material and coated with Sodium thermal insulation soft felt; the perforated plate is a perforated cylindrical cavity having a length of 2 cm and a diameter of 5.8 cm; and the perforated plate is filled with proppant particles of 40-60 meshes and uniformly formed with 100 hole channels with a diameter of 0.2 mm on the circular surface of the outer wall thereof.

3. The device for measuring a supercritical carbon dioxide fracturing fluid throttling coefficient under different viscosities according to claim 2, wherein the measurement pipeline segment is a copper coiler having an inner diameter of 4 mm, a wall thickness of 2 mm and a length of 8 m placed in the thermostatic water bath.

4. The device for measuring a supercritical carbon dioxide fracturing fluid throttling coefficient under different viscosities according to claim 3, wherein the supercritical carbon dioxide booster apparatus is provided with a carbon dioxide gas source inlet screwing valve; the thickening agent injection apparatus is provided with a thickening agent inlet screwing valve; the second pipeline is successively connected with the supercritical carbon dioxide booster apparatus and the thickening agent injection apparatus in a direction from the measurement pipeline segment to the constant speed and constant pressure pump; the measured data of the intermediate container pressure meter, the intermediate container thermometer, the first pressure meter, the first thermometer, the second pressure meter, the second thermometer and the first differential pressure sensor are collected by a data processing terminal in real time; and in the entire device, all the components and the pipelines are configured to withstand a pressure of 60 MPa and a temperature upper limit of 500 K, which are configured to realize experimental measurement of the supercritical carbon dioxide fracturing fluid throttling coefficient at a high temperature and under a high pressure.

5. A method for measuring a supercritical carbon dioxide fracturing fluid throttling coefficient using the device for measuring a supercritical carbon dioxide fracturing fluid throttling coefficient under different viscosities according to claim 4, wherein the method comprises the following steps:

creating a supercritical carbon dioxide cycle, comprising:
adjusting the thickening agent inlet screwing valve, a supercritical carbon dioxide fracturing fluid unloading screwing valve, the first screwing valve and the second screwing valve to be in a closed state; turning on the supercritical carbon dioxide booster apparatus, and adjusting the carbon dioxide gas source inlet screwing valve and the third screwing valve to be in an open state; and setting the thermostatic water bath to adjust the temperature and the pressure of the experimental system to be the temperature and the pressure set for the experiment;

adding a thickening agent, comprising:
turning on the thickening agent injection apparatus, opening the thickening agent inlet screwing valve, pumping the thickening agent into the supercritical carbon dioxide fracturing fluid viscosity adjustment apparatus, wherein the thickening agent and carbon dioxide flow under the action of a constant speed and constant pressure pump, and the thickening agent is completely dissolved into the supercritical carbon dioxide in a static mixer; after the parameter is stable, measuring the viscosity of the supercritical carbon dioxide fracturing fluid;

calculating the viscosity of the supercritical carbon dioxide fracturing fluid, comprising:
reading a pressure P of the intermediate container pressure meter, a temperature T of the intermediate container thermometer, a differential pressure $\Delta p$ of the first differential pressure sensor and the reading of a mass flow quantity Q of a mass flow meter from the data processing terminal, and calculating the viscosity $\mu$ of the supercritical carbon dioxide fracturing fluid:

$$\mu = \frac{uD\rho}{\text{Re}} \quad (1)$$

$$u = \frac{4Q}{\rho \pi D^2} \quad (2)$$

$$\rho = \rho_{CO_2} x_{CO_2} + \rho_t x_t \quad (3)$$

$$\rho_{CO_2} = \frac{PM_g}{ZRT} \quad (4)$$

$$Z^3 + (C-1)Z^2 + (A-2BC-B_2-C)Z + (BC+C-A)B = 0 \quad (5)$$

$$A = \frac{aP}{R^2T^2} \quad (6)$$

$$B = \frac{bP}{RT} \quad (7)$$

$$C = \frac{cP}{RT} \quad (8)$$

$$\frac{1}{\sqrt{\lambda}} = -2.34 \times \lg\left(\frac{\varepsilon}{1.72d} - \frac{9.26}{\text{Re}} \times \lg\left(\left(\frac{\varepsilon}{29.36D}\right)^{0.95} + \left(\frac{18.35}{\text{Re}}\right)^{1.108}\right)\right) \quad (9)$$

$$\lambda = \frac{2D\Delta p}{\rho u^2 L} \quad (10)$$

wherein $\mu$ is the viscosity of the supercritical carbon dioxide fracturing fluid, in Pa·s; u is the flow rate of the supercritical carbon dioxide fracturing fluid, in m/s; D is the diameter of a measurement pipeline segment, in m; $\rho$ is the density of the supercritical carbon dioxide fracturing fluid, in kg/m$^3$; Re is the Reynolds number of the supercritical carbon dioxide fracturing fluid, dimensionless; Q is the mass flow quantity of the supercritical fracturing fluid, in kg/s; $\rho_{CO_2}$ is the density of a supercritical carbon dioxide gas, in kg/m$^3$; $x_{CO_2}$ is the volume fraction of carbon dioxide in the fracturing fluid, dimensionless; $\rho_t$ is the density of the thickening agent, in kg/m$^3$; $x_t$ is the volume fraction of the thickening agent in the fracturing fluid, dimensionless; P is the pressure of the supercritical carbon dioxide gas, in MPa; $M_g$ is the molecular weight of the carbon dioxide, in kg/Kmol: Z is the compressibility factor of the supercritical carbon dioxide gas, dimensionless: R is the general gas constant 0.008314 MPa·m$^3$/(Kmol·K); T is the temperature of the supercritical carbon dioxide gas, in K; A, B and C are intermediate variables, the equations are as shown in formulae (6), (7) and (8), a=318101.19, b=26.82, c=25.01; λ is the coefficient of friction resistance of supercritical carbon dioxide, dimensionless; ε is the absolute roughness, in m; ΔP is the differential pressure measured by a measurement pipeline segment differential pressure sensor, in Pa; and L is the length of a measurement pipeline segment, in m;

measuring throttling coefficient $C_j$ of the supercritical carbon dioxide fracturing fluid, comprising:

closing the third screwing valve, opening the first screwing valve and the second screwing valve, setting the inlet pressure of the throttling apparatus by the constant pressure and constant speed pump, and setting the outlet back pressure by the back pressure control apparatus; after the parameter is stable, reading a pressure $p_1$ of the first pressure meter, a pressure $p_2$ of the second pressure meter, a temperature $T_1$ of the first thermometer and a temperature $T_2$ of the second thermometer from the data processing terminal, and calculating the throttling coefficient $C_j$ of the supercritical carbon dioxide fracturing fluid:

$$\Delta T' = T_1 - T_2 \quad (11)$$

$$\Delta p' = p_1 - p_2 \quad (12)$$

$$C_j = \frac{\Delta T'}{\Delta p'} \quad (13)$$

wherein $C_j$ the throttling coefficient of the supercritical carbon dioxide fracturing fluid, in K/Pa; $T_1$ is the temperature of the first thermometer, in K; $T_2$ is the temperature of the second thermometer, in K; $p_1$ is the pressure of the first pressure meter, in Pa; $p_2$ is the pressure of the second pressure meter, in Pa; ΔT' is the differential temperature before and after throttling, in K; Δp' is the differential pressure before and after throttling, in Pa.

* * * * *